United States Patent [19]

Atwell et al.

[11] Patent Number: 4,582,992

[45] Date of Patent: Apr. 15, 1986

[54] SELF-CONTAINED, ON-LINE, REAL-TIME BULK MATERIAL ANALYZER

[75] Inventors: Thomas L. Atwell, Del Mar; James F. Miller, Solana Beach; Ernesto A. Corte, La Jolla; Richard L. Conwell, Del Mar; Clinton L. Lingren, San Diego, all of Calif.

[73] Assignee: Gamma-Metrics, San Diego, Calif.

[21] Appl. No.: 639,577

[22] Filed: Aug. 10, 1984

[51] Int. Cl.[4] .......................................... G01N 23/222
[52] U.S. Cl. .............................. 250/359.1; 250/357.1; 250/358.1; 250/360.1; 250/390
[58] Field of Search ................. 250/358.1, 255, 390 C, 250/360.1, 359.1, 357.1, 356.1; 376/159; 378/45, 53

[56] References Cited

U.S. PATENT DOCUMENTS

| | | | |
|---|---|---|---|
| 3,064,357 | 11/1962 | Butters | 34/52 |
| 3,604,928 | 9/1971 | Starnes | 250/359.1 |
| 3,942,003 | 3/1976 | Apenberg et al. | 376/159 |
| 4,090,074 | 5/1978 | Watt et al. | 378/88 |
| 4,171,485 | 10/1979 | Marshall | 250/359.1 |
| 4,314,241 | 2/1982 | La Plante et al. | 340/603 |
| 4,362,939 | 12/1982 | Horiuchi et al. | 250/358.1 |

OTHER PUBLICATIONS

Harrison R. Cooper, "Progress in On-Line Coal Quality Measurement", CQ (Jan. 1984) pp. 16–23.
Kurt Yeager, "Nuclear Analysis of Coal", EPRI Journal (Jun. 1981) pp. 32–34.
A. Cekorich, H. Deich, T. Harrington and J. H. Marshall III, "Development of an Elemental Analyzer for Coal, Oil and Similar Bulk Streams—A Status Report" 1979 Symposium on Instrumentation and Control, Fossil Energy Processes, Denver, Co. (Aug. 1979), pp. 297–313.
Robert F. Stewart and A. W. Hall, "On Line Monitoring of Major Ash Elements in Coal Conversion Processes" The 13th Intersociety Energy Conversion Engineering Conference, Society of Automotive Engineers, Inc., Warrendale, Pa. (Oct. 1978), pp. 586–591.
NOLA 1 Data Sheet: "Neutron Activation Analysis for Industrial Process Control", Technical Specifications, Model NA 79), Texas Nuclear Division of Ramsey Engineering Company, Austin, TX (1979) 4 pages.

Primary Examiner—Alfred E. Smith
Assistant Examiner—C. Hannaher
Attorney, Agent, or Firm—Edward W. Callan

[57] ABSTRACT

A complete PGNAA bulk material analyzer is self contained in a sealed and air conditioned housing. Bulk material is channeled by an open-ended vertical chute having a one-foot-by-three-foot cross-sectional dimension through an activation region between three neutron sources and two gamma ray detectors. The sources are symmetrically disposed on one of the three-foot long sides of the chute from one end of such side to the other. The detectors are symmetrically disposed on the opposite side of the chute between positions opposing the positions of the sources on the one side of the chute. The chute is dimensioned to enable free flow of various bulk materials. It handles coal of up to a top size of four inches and with typical surface moisture contents and agglomeration characteristics. The relative disposition of the sources and detectors results in the measurements being independent of the lateral distribution of the bulk material within the chute. The signals produced by the detectors are continuously processed by signal processing equipment sealed within a separate compartment in the container to provide periodic measurements of the elemental content of the bulk material channeled through the activation region. A measurement of the bulk material channeled through the activation region during each periodic measurement interval is processed over several measurement intervals with the periodic elemental content measurements to provide weighted average measurements of the elemental content of bulk material over time periods representing average lots of the bulk material.

19 Claims, 4 Drawing Figures

SELF-CONTAINED, ON-LINE, REAL-TIME BULK MATERIAL ANALYZER

BACKGROUND OF THE INVENTION

The present invention pertains to improvement in bulk material analyzers.

Bulk material analyzers are used to measure the elemental content of bulk material. Such analyzers have been developed primarily to measure the quantitative content of materials, such as ash, in batches of coal, but also are useful for measuring the elemental content of the bulk materials. Such development is described in the following publications: Stewart and Hall, "On Line Monitoring of Major Ash Elements in Coal Conversion Process," Reprint 789671, October 1978, 13th Intersociety Energy Conversion Engineering Conference, Society of Automotive Engineer, Inc. Warrendale, Pa., pp 586–591; Cekorich et al "Development of an Elemental Analyzer for Coal, Oil and Similar Bulk Streams—A Status Report," 1979 Symposium on Instrumentation and Control Fossil Energy Processes, Aug. 20, 1979, Denver, Colo., pp 297–313; Yeager "R & D Status Report, Coal Combustion Systems Division," EPRI journal; June 1981, pp 32–24; Cooper, "Progress in On-Line Coal Quality Measurement," CQ, January 1984, pp 16–23; and NOLA 1 Data Sheet, "Neutron Activation Analysis for Industrial Process Control, Model NA 79," Texas Nuclear Division of Ramsey Engineering Company, Austin, Tex.

In a typical prior art bulk material analyzer, the bulk material is transported through an activation region between a radiation source and a gamma ray detector, and the detector produces signals which are processed to provide a measurement of the elemental content of the bulk material. Typically the radiation source is a neutron source. When the bulk material is bombarded by the radiation, secondary emissions of gamma rays are produced from the bulk material. Different characteristic gamma ray energy spectra are produced from different elements in the bulk materials. Accordingly by processing detected signals that are indicative of the gamma ray spectrum a measurement is provided of the elemental content of the bulk material. This measurement process is known in the art as prompt gamma ray neutron activation analysis (PGNAA).

In the system described by Stewart and Hall, which is also known as the Bureau of Mines system, the bulk material is fed through a hopper into a circular cross-section vertical chute. The radiation source is located within the vertical chute and the detector is located outside the chute at the same level as the radiation source.

In the Bureau of Mines system the strength of the signals produced by the detector is dependent upon the lateral distribution of the bulk material in the chute. Since bulk materials may exhibit gross segregation by particle size and density as they pass through the chute, the distribution of elemental content is generally quite inhomogenous. Thus there is a degree of inaccuracy in the measurements provided by processing the detector-produced signals. Such inaccuracy is proportional to the inhomogenity of the bulk material multiplied by the spatial nonuniformity of the detector response.

In the system described by Cekorich et al, which is known as the MDH system, the bulk material is channeled through the activation region by a relatively small vertical chute having an elongated rectangular cross-section of approximately 10 inches (25 cm) by 14 inches (35 cm); and two radiation sources are symmetrically disposed outside the chute on one of the long sides of the chute, and aligned normal to the long sides of the chute. A single detector is centered outside the other of the long sides of the chute between positions opposing the positions of the sources; and is aligned normal to the long sides of the chute. The symmetrical disposition of the two radiation sources and the detector tends to reduce the dependence of the detector-produced signals upon the lateral distribution of the bulk material within the chute. However, bulk material flow problems, such as plugging, bridging and segregation within the chute, occur in the MDH system, whereby particle top-size generally is limited to very dry particles that can pass through a minus two-inch (5 cm) mesh. As a result bulk materials such as coal must be crushed before they can be transported through the MDH system. The flow rate for coal is limited by the chute size to approximately thirty tons (27,000 Kg) per hour in the MDH system.

Bulk material analyzers typically are used at the bulk material processing or utilizing facilities. Knowledge of the elemental content is important to determining those operating parameters which will provide optimum material processing. For example, coal analysis enables knowledgeable blending of batches of coal having excessive ash and sulfur content with batches of a coal having lower contents of ash and sulfur. In the prior art of coal processing several discontinuous elemental-content measurements are made for each batch of coal. These measurements are averaged to provide an averaged weighted measurement. Using conventional ASTM sampling and analysis techniques, the desired information typically is not available for several hours.

In prior art on-line coal analyzers, the radiation source and the detector assembly are located around a chute or a conveyor and integrated into a permanent structure at the power plant. The signal processing equipment must be located in a separate enclosure or building in order to protect such equipment from dust and adverse local environmental conditions.

In summary, the prior art systems utilize various separate components and subassemblies that are installed in separate buildings or enclosures. Such systems are expensive to install and may be difficult to maintain. They also may require a large amount of space and expensive electrical cable interconnections between the separate buildings.

SUMMARY OF THE INVENTION

The present invention provides a self-contained, on-line, real-time bulk material analyzer, wherein the receptacle of the bulk material for analysis, the radiation source and the detector are integrated into a container that also houses the signal processing equipment. The present invention is a self-contained portable apparatus for measuring the elemental content of bulk material. The apparatus of the present invention includes a portable container; a radiation source within the container; a gamma ray detector within the container for detecting gamma rays secondarily emitted by materials that are bombarded by radiation from the source and for producing signals in response to the detected gamma rays; a receptacle for receiving bulk material in an activation region between the source and the detector, whereby the signals produced by the detector are characteristic of the elemental content of the received bulk material;

signal processing equipment within a separate compartment within the container for processing the produced signals to provide a measurement of the elemental content of the received bulk material; shielding material for shielding the separate compartment from radiation derived from the radiation source; sealing material for sealing the separate compartment from the environment outside the separate compartment to protect the processing equipment from dust and weather conditions outside the separate compartment; and a room within the container which may be entered by an operator, and which includes display panels and controls for operating the processing equipment. For most applications the apparatus necessarily further includes environmental conditioning equipment for maintaining a predetermined temperature range within the separate compartment.

Not only is there a considerable economic savings in combining all of the foregoing components into a single container, but the portability of the self-contained apparatus makes the bulk material analyzer easily removable and reusable at a new location after it is no longer required at an earlier location.

In accordance with another aspect of the present invention, the prior art inaccuracy-of-analysis problems caused by spatial nonuniformity of detector response are overcome by providing an apparatus in which the bulk material is received for analysis in an open-ended vertical chute having elongated rectangular cross section of approximately one foot (30 cm) by three feet (90 cm), which extends through the container for channeling bulk material fed from outside the container through the activation region and hence to outside the container; and wherein there are three of the radiation sources and two of the detectors. The chute is specifically dimensioned to eliminate the bulk material flow problems incident to the prior art MDH system; and the sources and detectors are relatively disposed for causing the measurements to be independent of the lateral distribution of the bulk material within the chute.

The cross-sectional dimensions of the chute provide plug free flow of bulk materials such as coals ranging in top size from a zero mesh to a minus four-inch (10 cm) mesh and having surface moisture characteristics typical of the majority of coals, including coals with a high surface moisture content and high agglomeration characteristics. Such dimensions also permit flow rates through the bulk material analyzer in excess of 500 tons (453,500 Kg) per hour for the majority of coals. Flow rates for bulk materials depend upon the flow characteristics of the material.

The three sources are symmetrically disposed on one of the three-foot long sides of the chute from one end of such side to the other end and aligned normal to the three-foot (90 cm) long sides of the chute. The two detectors are symmetrically disposed on the other of the three-foot (90 cm) long sides of the chute between positions opposing the positions of the sources on the one side of the chute, and aligned normal to the three-foot (90 cm) long sides of the chute.

In a further aspect of the present invention, wherein the bulk material is continuously transported through the activation region, and wherein the processing equipment continuously periodically provides a measurement of the elemental content of the transported bulk material as the bulk material is continuously transported through the activation region, the apparatus further includes equipment for measuring and indicating the mass of the bulk material transported through the activation region during each periodic measurement interval; and the processing equipment further processes the measured mass indications together with the elemental content measurements over several measurement intervals to provide a continuous weighted average measurement of the elemental content of the bulk material over time periods representing average lots of the bulk material. These continuous, real-time, weighted-average measurements are immediately available at the site of the portable bulk material analyzer of the present invention. As a result, batches of coal having different sulfur and ash contents can be blended on a timely basis and/or plant operating parameters can be quickly adjusted to optimize material processing.

The accuracy of the weighted-average measurements depends upon maintaining a nearly uniform cross-sectional density of bulk material within the activation region.

Preferably an input hopper is located at the top of a vertical chute for receiving bulk material that is channeled by the chute through the activation region. A nearly uniform cross-sectional density of the bulk material within the activation region is maintained for so long as the level of the bulk material within the hopper is maintained at least a predetermined minimum distance above the activation region. A sensor senses the level of the bulk material within the hopper. A controller is coupled to the sensor and to an apparatus for feeding the bulk material from the bottom of the hopper for controlling the feed rate in order to maintain the level of the bulk material within the hopper at least the predetermined minimum distance above the activation region. When the bulk material is coal, the minimum distance is approximately four feet (120 cm).

Additional features of the present invention are discussed in relation to the description of the preferred embodiment.

DESCRIPTION OF THE PREFERRED EMBODIMENT

Figure 1:
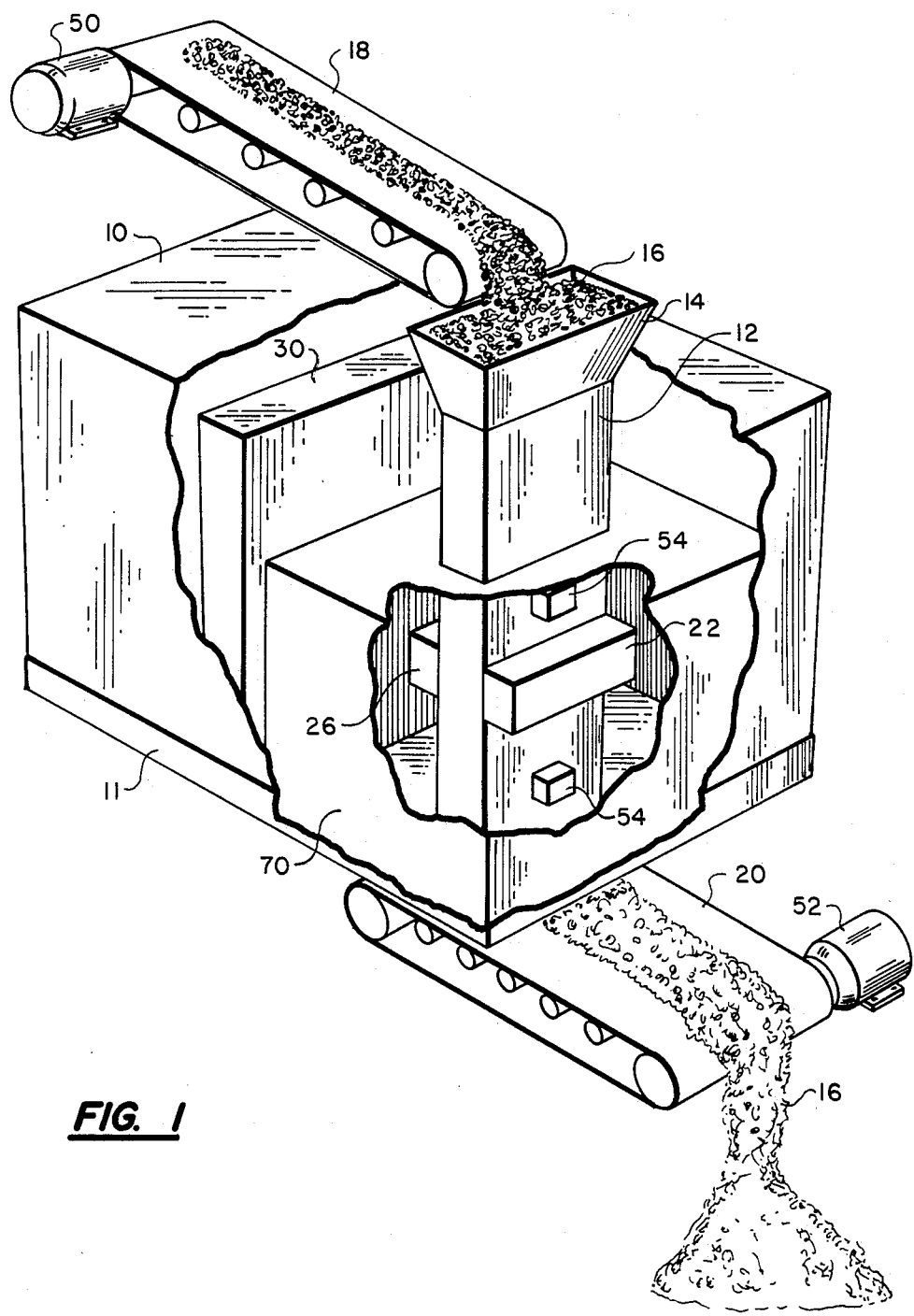
FIG. 1 is a partially cut away perspective view of a preferred embodiment of a portable bulk material analyzer according to the present invention.
Figure 2:
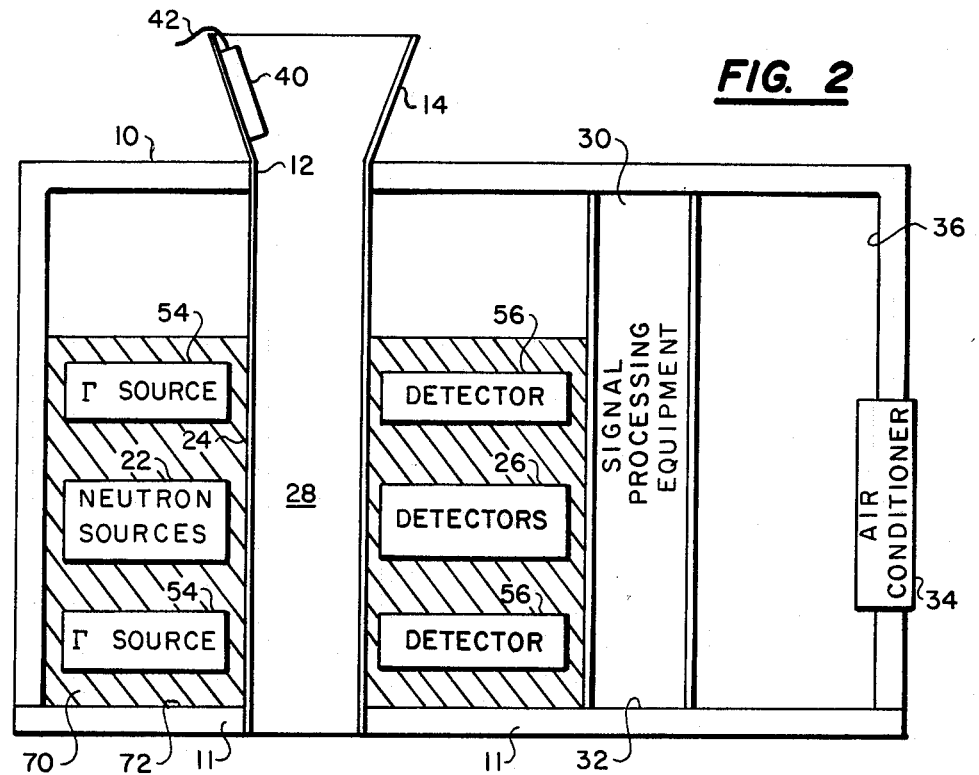
FIG. 2 is a cut-away side view of the bulk material analyzer of FIG. 1, including block diagrams indicating the location of certain radiation sources and detectors.
Figure 3:
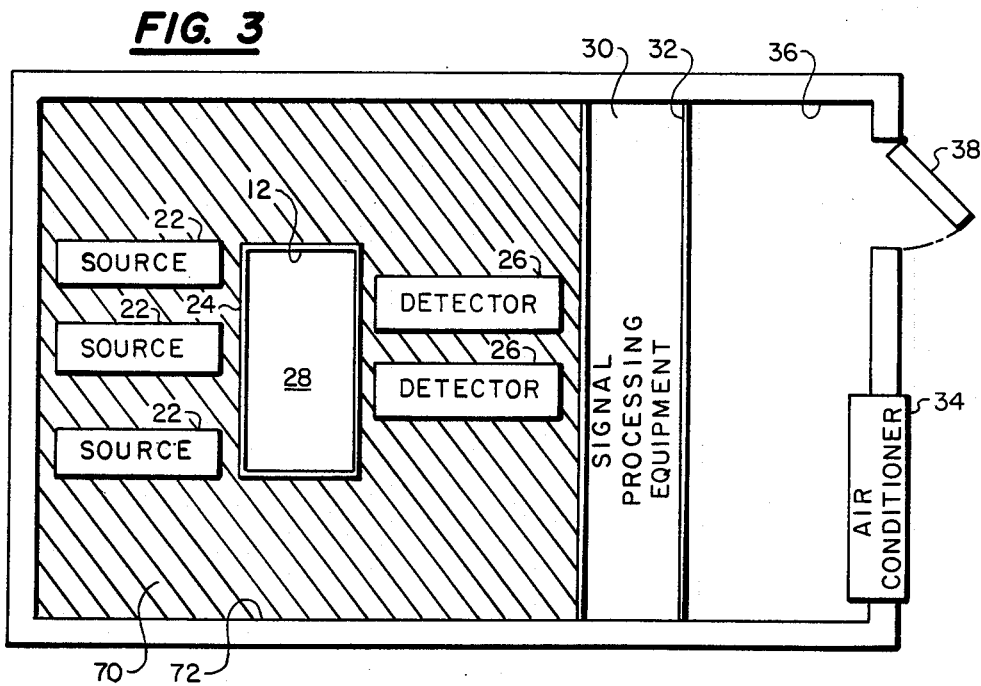
FIG. 3 is a cut-away top view of the bulk material analyzer of FIG. 1, including block diagrams showing the locations of the PGNAA radiation sources and detectors.

Referring to FIGS. 1, 2 and 3, the preferred embodiment of the bulk material analyzer of the present invention essentially includes a portable container 10. The container is approximately eight feet wide (240 cm) by ten feet (300 cm) long by eight feet (240 cm) high. The dimensions stated herein are particularly applicable to a coal analyzer and may differ for analyzers of other types of bulk materials in accordance with the physical characteristics of the bulk material, such as flowability.

The bottom 11 of the container 10 is a steel platform which is equipped with mounting pads (not shown) on the underside. The container 10 can be lifted for movement from one installation to another.

An open-ended vertical chute 12 extends through the container 10. An input hopper 14 is fastened to the top of the chute 12 for receiving bulk material 16 that is channeled through the chute 12. The bulk material 16, such as coal, is fed into the hopper 14 by an input conveyor 18 and is fed away from the bottom of the chute 12 by an output conveyor 20.

The chute 12 is particularly dimensioned in accordance with the flow characteristics of coal; and thereby has a rectangular cross section of approximately one foot (30 cm) by three feet (90 cm) to assure that coal which is up to 4-inch (10 cm) top size will flow therethrough without plugging or bridging within the chute 12. It has been found that coal can be channeled through a chute of these dimensions without having to first crush, riffle and dry the coal.

Three neutron radiation sources 22 are symmetrically disposed on and outside one of the three-foot (90 cm) long sides of chute 12 from one end of the one side 24 to the other end. The sources 22 are aligned (directionally collimated) normal to the three-foot (90 cm) long sides of the chute 12.

Two gamma ray detectors 26 are symmetrically disposed on and outside the other of the three-foot (90 cm) long sides of the chute between positions opposing the positions of the sources 22 on the one side 24 of the chute 12. The detectors 26 are aligned (directionally collimated) normal to the three-foot (90 cm) long sides of the chute 12.

The sources 22 and the detectors 26 are aligned in a common plane which is approximately three feet (90 cm) above the bottom of the chute 12. The region between the sources 22 and the detectors 26 is referred to herein as the activation region 28.

The detectors 26 detect gamma rays that are secondarily emitted by materials in the activation region 28 that are bombarded by neutron radiation from the sources 22. The detectors 26 produce signals in response to the detected gamma rays. These produced signals are characteristic of the elemental content of the bulk material in the activation region 28.

The three sources 22 and two detectors 26 are relatively disposed as described above for causing the measurements to be independent of the lateral distribution of the bulk material 16 in the chute 12.

The bulk material analyzer further includes signal processing equipment 30 for combining and processing the signals produced by the detectors 26 to provide a measurement of the elemental content of the bulk material that is channeled through the activation region 28 by the chute 12. The signal processing equipment 30 is located within a separate compartment 32 within the container 10. The separate compartment 32 is sealed from the environment outside the separate compartment 32 to protect the signal processing equipment 30 from dust and weather conditions outside the separate compartment 32.

The container 10 further includes an air conditioner 34 which is coupled to the separate compartment 32 by ducts (not shown) for maintaining a predetermined temperature range within the separate compartment 32.

The container 10 further includes a room 36 which may be entered by a door 38 to admit an operator. The room 36 includes display panels and controls (not shown) for operating the signal processing equipment 30 and connection points for remote display panels and controls.

In order to maintain a nearly uniform cross-sectional density of bulk material 16 in the activation region 28 within the chute 12, it is necessary to maintain the level of the bulk material 16 within the hopper 14 at least a predetermined minimum distance above the activation region 28. When the bulk material is coal, for a chute having a one-foot (30 cm) by three-foot (90 cm) cross sectional dimension, this predetermined minimum distance is approximately four feet (120 cm).

A level sensor 40 is positioned in the hopper 14 for sensing the level of the bulk material within the hopper 14. The level sensor 40 provides a signal on line 42 to flow rate controller 44 (FIG. 4), which in turn provides control signals on lines 46 and/or 48 to motors 50 and 52 which respectively drive the input conveyor 18 and the output conveyor 20 at a variable rate in accordance with the control signals provided on lines 46 and 48. The flow rate controller 44 controls the feed rate of the output conveyor 20 to maintain the level of the bulk material 16 within the hopper 14 at least the predetermined minimum distance above the activation region 28 in order to maintain a nearly uniform cross-sectional density of bulk material 16 within the activation region.

The flow rate controller 44 may control the feed rate of the input conveyor 18 to be approximately the same as that of the output conveyor 20 so as to maintain a continuous flow of bulk material through the chute 12.

The flow rate controller 44 further responds to the signal on line 42 from the level sensor 40 by controlling the feed rate of the conveyors 18, 20 to prevent the level of the bulk material 16 in the hopper 14 from exceeding a predetermined maximum level.

The signal processing equipment continuously processes the signals produced by the detectors 26 to provide periodic measurements of the elemental content of the bulk material 16 channeled through the activation region 28 by the chute 12. In the preferred embodiment these measurements are provided every one minute. The signal processing equipment 30 further provides a weighted average measurement of the elemental content of the bulk material over time periods representing average lots of the bulk material. To perform this function a measurement is made of the mass of bulk material 16 transported through the activation region 28 during each periodic measurement interval. To make this measurement of mass, measurements are made of the flow rate and density of the bulk material being channeled through the chute 12.

Density gauges are located adjacent the chute 12 approximately equidistant above and below the activation region 28. Each density gauge includes a gamma ray radiation source 54 and a gamma ray detector 56. The detectors provide signals indicating the density of the bulk material in the chute 12 and are hereinafter referred to as "density detectors" 56. The detectors 26 adjacent the activation region 28 are hereinafter referred to as "PGNAA detectors" 26.

Figure 4:
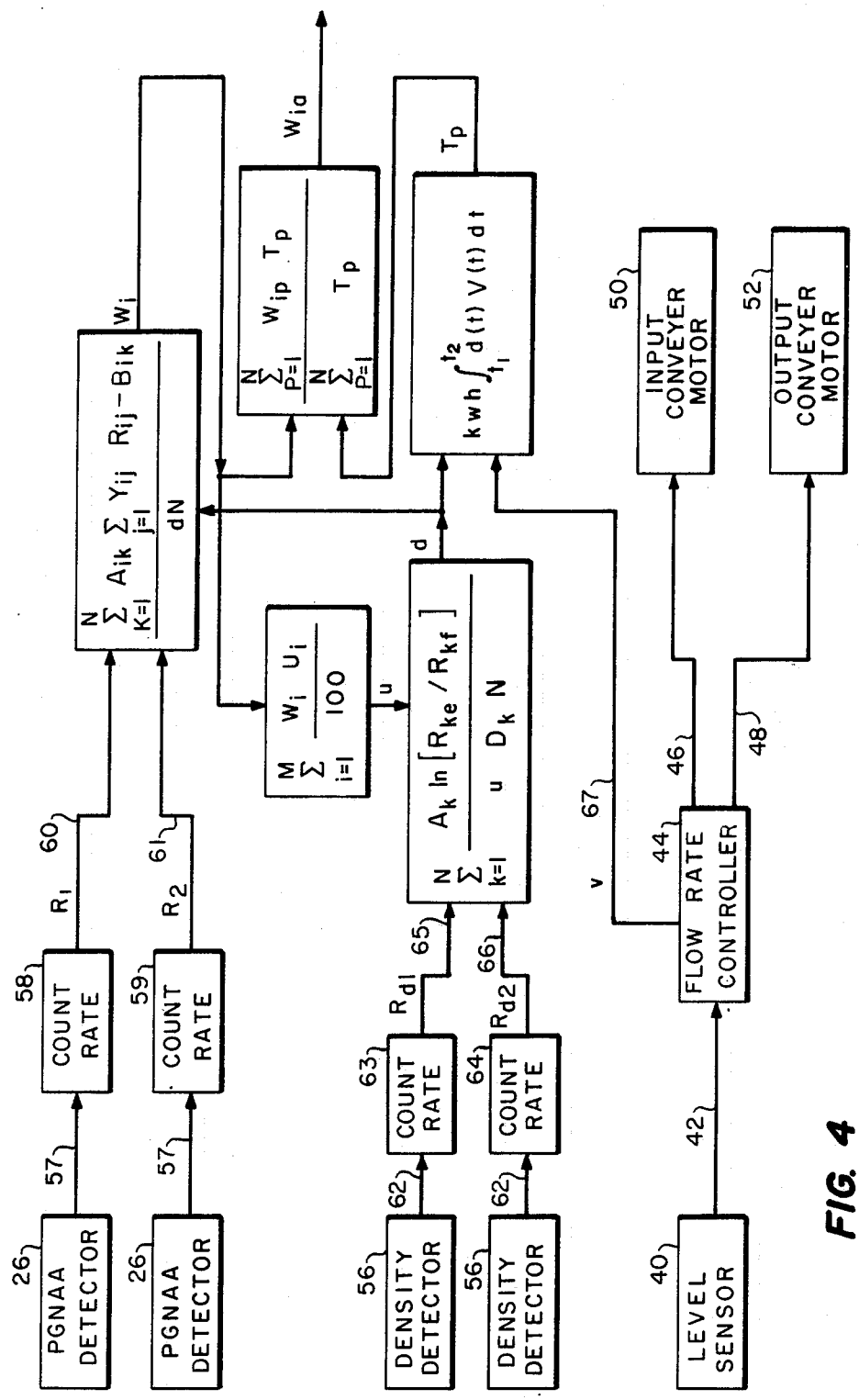
FIG. 4 is a block diagram illustrating the processing and control functions of the signal processing equipment in the bulk material analyzer of FIG. 1.

Referring to FIG. 4, the signals produced by the two PGNAA detectors 26 are provided on lines 57 to count rate circuits 58 and 59 which provide PGNAA count rate signals $R_1$ and $R_2$ on lines 60 and 61 respectively. The signals produced by the two density detectors 56 are provided on lines 62 to count rate circuits 63 and 64 which provide density count rate signals $R_{d1}$ and $R_{d2}$ on lines 65 and 66 respectively.

The flow rate controller 44 provides a velocity signal V on line 67 to indicate the feed rate of the output conveyor 20, which corresponds to the flow rate of the bulk material 16 through the chute 12.

The signal processing equipment 30 processes the PGNAA count rate signals $R_1$ and $R_2$ on lines 60 and 61, the density count rate signals $R_{d1}$ and $R_{d2}$ on lines 65 and 66 and the velocity signal on line 67 to provide a weighted average measurement $W_{ia}$ of the elemental content of the bulk material over measurement intervals $P = t_2 - t_1$, as shown in FIG. 4.

The elemental content measurement $W_i$ is provided by processing the PGNAA count rate signals $R_1$ and $R_2$ on lines 60 and 61 together with an internally provided bulk material density measurement "d" in accordance with the following equation:

$$W_i = \left[ \sum_{k=1}^{N} A_{ik} \sum_{j=1}^{M} Y_{ij} R_{ij} - B_{ik} \right] / [dN] \quad \text{(Equation 1)}$$

where:

i = Element index;
j = Major gamma ray energies associated with element i;
k = PGNAA detector index;
$W_i$ = Percent by weight of element i in the total bulk material;
d = The density of the total bulk material;
N = Number of PGNAA detectors;
$Y_{ij}$ = Yield factor of element i for production of gamma rays j which can be detected by the PGNAA detectors and discerned by the count rate circuits 58, 59 per unit of neutron source strength. The yield factor $Y_{ij}$ is the product of the reaction probability factor for element i to emit prompt gamma rays j upon stimulus of a neutron source, the detector intrinsic and geometrical efficiency factors for gamma rays from element i, and any material attenuation factors influencing the transmission of the gamma rays j from the point of creation in the bulk material to the detector;
$R_{ij}$ = Net count rate of gamma rays of energy j detected by the PGNAA detectors and discerned by the count rate circuits 58, 59 as possessing energy j and as emanating from element i;
$A_{ik}$ = Product of the overall system calibration factor from element i including effective neutron source of strength; and
$B_{ik}$ = Element offset factor to account for the contribution of the measured signal from those elements which are also present in the constituents of the coal analyzer which surround the chute in the vicinity of the bulk material being measured.

Both $A_{ik}$ and $B_{ik}$ are determined by measuring bulk material standards and performing least square fit of the known weight percent of composite elements to the measured responses $W_i$ of composite elements.

The density "d" measurement is provided by processing the density count rate signals $R_{d1}$ and $R_{d2}$ on lines 65 and 66 together with an internally provided indications "u" of the mean mass attenuation coefficient for the bulk material being measured in accordance with the following equation:

$$d = \sum_{k=1}^{N} \frac{A_k \ln [R_{ke}/R_{kf}]}{uDN}, \quad \text{(Equation 2)}$$

where:

$R_{kf}$ = Count rate measured by density detector k when bulk material is present in the chute;
$R_{ke}$ = Count rate measured by density detector k when vertical chute is void of all material;
N = Number of density detectors;
$A_k$ = Overall calibration constant for density gauge k including Compton Scattering buildup factor;
D = Inside dimensions of vertical chute between density detector 56 and gamma ray source 54 for density gauge k; and
u = Mean mass attenuation coefficient for the bulk material being measured.

Coefficient "u" indication is provided by processing the elemental content measurements $W_i$ in accordance with the following equation:

$$u = \sum_{i=1}^{M} \frac{W_i U_i}{100}, \quad \text{(Equation 3)}$$

where:

$W_i$ = Weight percent of the element i;
$U_i$ = Known mass attenuation coefficient for element i at the energy of the density gauge source gamma rays.

A periodic measurement $T_p$ of the mass of the bulk material is provided by periodically processing the density indication d and the velocity signal V on line 67 over a measurement interval $p = t_2 - t_1$ in accordance with the following equation:

$$T_p = KWh \int_{t_1}^{t_2} d(t) V(t) dt \quad \text{(Equation 4)}$$

where:

d(t) = Bulk material density over the interval $t_1$ to $t_2$;
V(t) = Linear speed of output conveyor;
W = Width of bulk material loading on the output conveyor;
h = Height of bulk material loading on the output conveyor; and
K = Calibration factor to compensate for the differences between density as measured in the chute and density of bulk material on the output conveyor.

Equation 4 is applicable only if the level of the bulk material 16 in the hopper 14 is maintained at least the aforementioned predetermined distance above the activation region 28.

The weighted average measurement $W_{ia}$ of the elemental content of the bulk material over a time period $N_p$ representing an average lot of bulk material is provided by processing the measured periodic mass indication $T_p$ together with the elemental content measurements $W_i$ in accordance with the following equation:

$$W_{ia} = \sum_{p=1}^{N} W_{ip} T_p / \sum_{p=1}^{N} T_p \quad \text{(Equation 5)}$$

where:

$W_{ip}$ = Weight percentage for element i determined during measurement interval p;
$T_p$ = Mass of bulk material measured during interval p; and
N = Number of measurement intervals p.

The signal processing equipment further processes the weighted average measurements of the elemental content of the bulk material to provide measurements of the bulk material characteristics.

Referring again to FIGS. 1, 2 and 3, a radiation shielding material 70 fills the volume of the compartment 72 within the container 10 surrounding the chute 12, the neutron sources 22, the gamma ray sources 54, the PGNAA detectors 26 and the density detectors 56 up to a height above the upper density gauge. The shielding material 70 shields the separate compartment 32 and the signal processing equipment 30 therein from radiation derived either primarily or secondarily from the radiation sources 22 and 54.

The compartment 72 is sealed from the environment outside the container 10 to protect the radiation sources 22, 54 and detectors 26, 56 from dust and weather conditions outside the container and from damage resulting from contact with the bulk material 16.

We claim:

1. A self-contained, portable apparatus for measuring the elemental content of bulk material, comprising;
    a portable container;
    a radiation source within the container;
    a gamma ray detector within the container for detecting gamma rays secondarily emitted by materials that are bombarded by radiation from the source and for producing signals in response to the detected gamma rays;
    means for receiving bulk material in an activation region between the source and the detector, whereby said produced signals are characteristic of the elemental content of said received bulk material;
    means within a separate compartment within the container for processing said produced signals to provide a measurement of the elemental content of said received bulk material;
    means for shielding the separate compartment from radiation derived from the radiation source;
    means for sealing the separate compartment from the environment outside the separate compartment to protect the processing means from dust and weather conditions outside the separate compartment; and
    a room within the container which may be entered by a door to admit an operator, and which includes display panels and controls for operating the processing means.

2. An apparatus according to claim 1, further comprising means for maintaining a predetermined temperature range within the separate compartment.

3. An appparatus according to claim 2, further comprising means for sealing the radiation source and the detector from the bulk material and the environment outside the container to protect the radiation source and the detector from dust, weather conditions outside the container and from damage resulting from contact with the bulk material.

4. A self-contained, portable apparatus for measuring the elemental content of bulk material, comprising;
    a portable container;
    a radiation source within the container;
    a gamma ray detector within the container for detecting gamma rays secondarily emitted by materials that are bombarded by radiation from the source and for producing signals in response to the detected gamma rays;
    means for receiving bulk material in an activation region between the source and the detector, whereby said produced signals are characteristic of the elemental content of said received bulk material;
    means within a separate compartment within the container for processing said produced signals to provide a measurement of the elemental content of said received bulk material;
    means for shielding the separate compartment from radiation derived from the radiation source; and
    means for sealing the separate compartment from the environment outside the separate compartment to protect the processing means from dust and weather conditions outside the separate compartment;
    wherein the means for receiving the bulk material comprises
    an open-ended vertical chute through the container for channeling bulk material fed from outside the container through the activation region and hence to outside the container.

5. An apparatus according to claim 1, further comprising means for sealing the radiation source and the detector from the bulk material and the environment outside the container to protect the radiation source and the detector from dust, weather conditions outside the container and from damage resulting from contact with the bulk material.

6. A self-contained, portable apparatus for measuring the elemental content of bulk material, comprising;
    a portable container;
    a radiation source within the container;
    a gamma ray detector within the container for detecting gamma rays secondarily emitted by materials that are bombarded by radiation from the source and for producing signals in response to the detected gamma rays;
    means for receiving bulk material in an activation region between the source and the detector, whereby said produced signals are characteristic of the elemental content of said received bulk material;
    means within a separate compartment within the container for processing said produced signals to provide a measurement of the elemental content of said received bulk material;
    means for shielding the separate compartment from radiation derived from the radiation source; and
    means for sealing the separate compartment from the environment outside the separate compartment to protect the processing means from dust and weather conditions outside the separate compartment;
    wherein the means for receiving the bulk material comprises
    an open-ended chute having an elongated rectangular cross-section of approximately one foot (30 cm) by three feet (90 cm) for channeling bulk material fed from outside the container through the activation region and hence to outside the container; and
    wherein the apparatus comprises three of said radiation source and two of said detectors, wherein the sources and detectors are relatively disposed for causing the measurement to be independent of the lateral distribution of the bulk material within the chute, to wit:
    the three sources are symmetrically disposed on one of the three-foot (90 cm) long sides of the chute from one end of said one side to the other and aligned normal to the three-foot (90 cm) long sides of the chute; and the two detectors are symmetrically disposed on the other of the three-foot (90 cm) long sides of the chute between positions opposing the positions of the sources on the one side of the chute, and aligned normal to the three-foot (90 cm) long sides of the chute.

7. An apparatus according to claim 6, wherein the processing means continuously processes the produced signals to provide periodic measurements of said elemental content of said bulk material;

wherein the apparatus further comprises means for measuring and indicating the mass of said bulk material channeled through the activation region during each periodic measurement interval; and wherein the processing means further processes said measured mass indications together with said elemental content measurements over several measurement intervals to provide a weighted average measurement of the elemental content of said bulk material over time periods representing average lots of the bulk material.

8. An apparatus according to claim 7, further comprisisng an input hopper at the top of the chute for receiving the bulk material that is channeled through the chute;

means for sensing the level of the bulk material within the hopper;

means for feeding said bulk material from the bottom of the chute at a variable rate;

means coupled to the sensing means and the feed means for controlling the feed rate of the feed means to maintain the level of the bulk material within the hopper at least a predetermined minimum distance above the activation region in order to maintain a nearly uniform cross-sectional density of bulk material within the activation region.

9. An apparatus according to claim 8, wherein the bulk material is coal; and wherein the predetermined minimum distance is approximately four feet (120 cm).

10. An apparatus according to claim 1, wherein the means for receiving the bulk material comprises means for continuously transporting the bulk material through the activation region wherein the processing means continuously processes the produced signals as the bulk material is continuously transported through the activation region to provide period measurements of said elemental content of said bulk material;

wherein the apparatus further comprises means for measuring and indicating the mass of said bulk material transported through the activation region during each periodic measurement interval; and wherein the processing means further processes said measured mass indications together with said elemental content measurements over severval measurement intervals to provide a weighted average measurement of the elemental content of said bulk material over time periods representing average lots of said bulk material.

11. An apparatus according to claim 10, wherein the transporting means comprises an open-ended vertical chute through the container for channeling bulk material fed from outside the container through the activation region and hence to outside the container; and wherein the apparatus further comprises an input hopper at the top of the chute for receiving the bulk material that is channeled through the chute;

means for sensing the level of the bulk material within the hopper;

means for feeding said bulk material from the bottom of the chute at a variable rate;

means coupled to the sensing means and the feed means for controlling the feed rate of the feed means to maintain the level of the bulk material within the hopper at least a predetermined minimum distance above the activation region in order to maintain a nearly uniform cross-sectional density of bulk material within the activation region.

12. An apparatus according to claim 11, wherein the bulk material is coal; and wherein the predetermined minimum distance is approximately four feet (120 cm).

13. An apparatus for measuring the elemental content of bulk material, comprising three radiation sources;

two gamma ray detectors for detecting gamma rays secondarily emitted by materials that are bombarded by radiation from the source, and for producing signals in response to the detected gamma rays;

an open-ended vertical chute having an elongated rectangular cross-section of approximately one foot (30 cm) by three feet (90 cm) for channeling bulk material through an activation region between the radiation sources and the detectors whereby the combined signal is characteristic of the elemental content of said channeled bulk material; and means for processing said produced signals to provide a measurement of the elemental content of said channeled bulk material;

wherein the sources and detectors are relatively disposed for causing the measurement to be independent of the lateral distribution of the bulk material within the chute, to wit:

the three sources are symmetrically disposed on one of the three-foot (90 cm) long sides of the chute from one end of said one side to the other end and aligned normal to the three-foot (90 cm) long sides of the chute; and the two detectors are symmetrically disposed on the other of the three-foot (90 cm) long sides of the chute beiween positions opposing the positions of the sources on the one side of the chute, and aligned normal to the three-foot (90 cm) long sides of the chute.

14. An apparatus according to claim 13, wherein the processing means continuously processes the produced signals to provide periodic measurements of said elemental content of said bulk material;

wherein the apparatus further comprises means for measuring and indicating the mass of said bulk material channeled through the activation region during each periodic measurement interval; and wherein the processing means further processes said measured mass indications together with said elemental content measurements over several measurement intervals to provide a weighted average measurement of the elemental content of said bulk material over time periods representing average lots of the bulk material.

15. An apparatus according to claim 14, further comprising
- an input hopper at the top of the chute for receiving the bulk material that is channeled through the chute;
- means for sensing the level of the bulk material within the hopper;
- means for feeding said bulk material from the bottom of the chute at a variable rate;
- means coupled to the sensing means and the feed means for controlling the feed rate of the feed means to maintain the level of the bulk material within the hopper at least a predetermined minimum distance above the activation region in order to maintain a nearly uniform cross-sectional density of bulk material within the activation region.

16. An apparatus according to claim 15, wherein the bulk material is coal; and
- wherein the predetermined minimum distance is approximately four feet (120 cm).

17. An apparatus for measuring the elemental content of bulk material, comprising
- a radiation source;
- a gamma ray detector for detecting gamma rays secondarily emitted by materials that are bombarded by radiation from the source and for producing signals in response to the detected gamma rays;
- means for continuously transporting bulk material through an activation region between the source and the detector, whereby said produced signals are characteristic of the elemental content of said transported bulk material;
- means for continuously processing said produced signals as the bulk material is continuously transported through the activation region to provide periodic measurements of the elemental content of said transported bulk material; and
- means for measuring and indicating the mass of said bulk material transported through the activation region during each periodic measurement interval;
- wherein the processing means further processes said measured mass indications together with said elemental content measurements over several measurements intervals to provide a weighted average measurement of the elemental content of said bulk material over time periods representing average lots of said bulk material.

18. An apparatus according to claim 17,
- wherein the transporting means comprises an open-ended vertical chute through the container for channeling bulk material fed from outside the container through the activation region and hence to outside the container; and
- wherein the apparatus further comprises an input hopper at the top of the chute for receiving the bulk material that is channeled through the chute;
- means for sensing the level of the bulk material within the hopper;
- means for feeding said bulk material from the bottom of the chute at a variable rate;
- means coupled to the sensing means and the feed means for controlling the feed rate of the feed means to maintain the level of the bulk material within the hopper at least a predetermined minimum distance above the activation region in order to maintain a nearly uniform cross-sectional density of bulk material within the activation region.

19. An apparatus according to claim 18, wherein the bulk material is coal; and
- wherein the predetermined minimum distance is approximately four feet (120 cm).

* * * * *